United States Patent
Batteux et al.

(10) Patent No.: US 7,351,722 B2
(45) Date of Patent: Apr. 1, 2008

(54) USE OF MANGAFODIPIR FOR TREATING OXIDATIVE STRESS EFFECTS

(75) Inventors: Frederic Batteux, Paris (FR); Bernard Weill, Eaubonne (FR)

(73) Assignee: Universite Rene Descartes (Paris V), Paris (FR)

( * ) Notice: Subject to any disclaimer, the term of this patent is extended or adjusted under 35 U.S.C. 154(b) by 176 days.

(21) Appl. No.: 10/475,555

(22) PCT Filed: Apr. 26, 2002

(86) PCT No.: PCT/FR02/01457

§ 371 (c)(1),
(2), (4) Date: Oct. 22, 2003

(87) PCT Pub. No.: WO02/087579

PCT Pub. Date: Nov. 7, 2002

(65) Prior Publication Data

US 2004/0142907 A1 Jul. 22, 2004

(30) Foreign Application Priority Data

Apr. 26, 2001 (FR) .................................. 01 05606

(51) Int. Cl.
*A61K 31/44* (2006.01)
(52) U.S. Cl. .................................................... 514/332
(58) Field of Classification Search ................. 514/332
See application file for complete search history.

(56) References Cited

FOREIGN PATENT DOCUMENTS

| WO | 97 49409 | 12/1997 |
|----|----------|---------|
| WO | 99 33521 | 7/1999 |

OTHER PUBLICATIONS

Yicheng et al., "Experimental Liver Cancers: Mn-DPDP-enhanced Rims in MR-Microantiographic-Histologic Correlation Study" Radiology 1993; 188:45-51.*

Stedman's Medical Dictionary, 27th Edition [online], retrieved on Jan. 3, 2005, retrieved from http://pdrel.thomsonhc.com/pdrel/librarian/PFDefaultActionId/pdrcommon.Stedmans (definition of "patient").*

Stedman's Medical Dictionary, 27th Edition [online], retrieved on Jan. 3, 2005, retrieved from http://pdrel.thomsonhc.com/pdrel/librarian/PFDefaultActionId/pdrcommon.Stedmans (definition of "carcinoma").*

Stedman's Medical Dictionary, 27th Edition [online], retrieved on Jan. 3, 2005, retrieved from http://pdrel.thomsonhc.com/pdrel/librarian/PFDefaultActionId/pdrcommon.Stedmans (definition of "parenteral").*

Cecil, Textbook of Medicine, 21st Edition, vol. 1, published 2000 by W.B. Saunders Company (Philadelphia), pp. 815 and 817.*

Heidi Brurok et al.: "Manganese dipyridoxyl diphosphate: MRI contrast agent with antioxidative and cardioprotective properties? in vitro and ex vivo assessments" Biochem. Biophys. Res. Commun., vol. 254, No. 3, pp. 768-772, 1999.

G. Marchal et al.: "Comparison between gadolinium-DTPA, gadolinium-EOP-DPTA, and manganese-DPDP in induced HCC in rats: a correlation study of MR imaging" Magn. Reson. Imaging, vol. 11, No. 5, pp. 665-674, 1993.

M. Oudkerk et al.: "Better liver lesion diagnosis with mangafodipir trisodium (MnDPDP)-enhanced MR liver imaging: A multicenter study comparing MR and biphasic spiral CT" Journal of Hepatology, vol. 32, No. Supplement 2, apge 136, 2000.

A. Asplund et al.: "Mangafodipir (MnPDP)-and MNCL2-induced endothelium-dependent relaxation in bovine mesenteric arteries 1" Journal of Pharmacology and Experimental Therapeutics, vol. 271, No. 2, pp. 609-614, Nov. 1, 1994.

Stuart W. Young et al.: "Detection of hepatic malignancies using manganese-DPDP (manganese dipyridoxal diphosphate) hepatobiliary MRI contrast agent" Magn. Reson. Imaging, vol. 8, No. 3, pp. 267-276, 1990.

A. Graul et al.: "Mangafodipir trisodium" Drugs Future, vol. 22, No. 9, pp. 974-979 1997.

* cited by examiner

*Primary Examiner*—Raymond J. Henley, III
(74) *Attorney, Agent, or Firm*—Oblon, Spivak, McClelland, Maier & Neustadt, P.C.

(57) ABSTRACT

The invention concerns the use of Mangafodipir to obtain a medicine for preventive or curative treatment of hepatocellular deficiencies.

13 Claims, 4 Drawing Sheets

USE OF MANGAFODIPIR FOR TREATING OXIDATIVE STRESS EFFECTS

The invention relates to the use of Mangafodipir in the context of the treatment of hepatocellular deficiencies.

Manganese dipyridoxyl phosphate (Mn-DPDP), also referred to as Mangafodipir (INN), is used in radiology as a paramagnetic contrast product in the context of diagnosis by MRI (magnetic resonance imaging); for review on the properties of Mangafodipir, cf. Rocklage et al., Inorg. Chem., 28, 477-485, (1989).

Some pharmacological properties of Mangafodipir have also been reported: Asplund et al., (J. Pharmacol. Exp. Therapeutics, vol. 271, no. 2, p. 609-614, 1994) describe its vasodilatory properties, which are attributed to an effect of stabilizing the nitric oxide produced by the cells of the vascular endothelium; these authors indicate that this effect might ensue from an activity of the superoxide dismutase (SOD) type. Brurok et al. (Biochem. Biophys. Res. Commun., vol. 254, no. 3, p. 768-772, 1999) have observed, in vitro, its properties as an SOD mimetic, resulting, ex vivo, in a cardioprotective action with respect to the effects of the oxygenated free radicals $O_2^-$ and $OH^-$ generated during hypoxia followed by reoxygenation. PCT application WO 97/49409 proposes the use of Mangafodipir or of other dipyridoxyl-derived or aminopolycarboxylic acid-derived chelating agents in the context of the treatment of pathological conditions induced by free radicals, namely the damage resulting from ischemia-reperfusion, occurring in particular during infarction or other cardiovascular diseases, or pro-inflammatory pathological conditions such as the damage induced by radiation. PCT application WO 99/33521 proposes the use of these same chelating agents for treating atherosclerosis, by preventing the oxidation of LDLs (low density lipoproteins), or as cytotoxic agents for treating infections with bacteria or protozoa, or as detoxifying agents for treating poisoning with metals such as iron.

The various therapeutic uses of Mangafodipir proposed above ensue mainly from its properties as a superoxide dismutase mimetic. Superoxide dismutase (EC 1.15.1.1) is involved in the detoxification of oxygenated free radicals, by catalyzing the dismutation of the superoxide anion ($O_2^-$) to hydrogen peroxide ($H_2O_2$). Various types of superoxide dismutase are distinguished, among which mention will in particular be made of copper/zinc superoxide dismutases (CuZnSOD), also known as superoxide dismutase-1, which, in eukaryotic organisms, are mainly located in the cytoplasm, and manganese superoxide dismutases (MnSOD), also known as superoxide dismutase-2, which are mainly found in prokaryotes and in the intracellular organelles of eukaryotic cells.

The use of SOD mimetics has been proposed in the context of various pathological conditions involving an oxidative stress caused by oxygenated free radicals [for review cf. Patel and Day, Trends Pharmacol. Sci., 20, 359-364 (1999)]. However, they do not have an equal effect on all pathological conditions.

Thus, in prior studies relating to hepatocellular deficiency, which is one of the many pathological conditions in which a potential role for oxygenated free radicals has been mentioned, the inventors observed that a mimetic of CuZnSOD, CuDIPS (Cu[II]-[diisopropylsalicylate]), had no significant effect; on the other hand, they noted that a mimetic of MnSOD, MnTBAP [Mn(III)-tetrakis(5,10,15,20-benzoic acid)-porphyrin], also having catalase activity and glutathione peroxidase activity, had a notable preventive and curative effect (Application PCT/WO 01/12327; Ferret et al., Hepatology, vol. 33, no. 5, p. 1173-1180, May 2001).

This effectiveness of MnTBAP might be explained by its catalase and glutathione peroxidase activities, which would supplement its SOD activity by allowing detoxification of the hydrogen peroxide generated by dismutation of the superoxide anion.

To verify this hypothesis, the inventors undertook a search for other SOD mimetics having activities for detoxifying reactive oxygenated species other than the superoxide anion, and tested their effect on hepatocellular deficiency.

They thus noted that, unlike what had previously been reported (Brurok et al., 1999, mentioned above), Mangafodipir, like MnTBAP, had catalase activity, and that it also had glutathione reductase activity. They also observed that its effectiveness with respect to hepatocellular deficiency was at least equal to that of MnTBAP.

Figure 1:
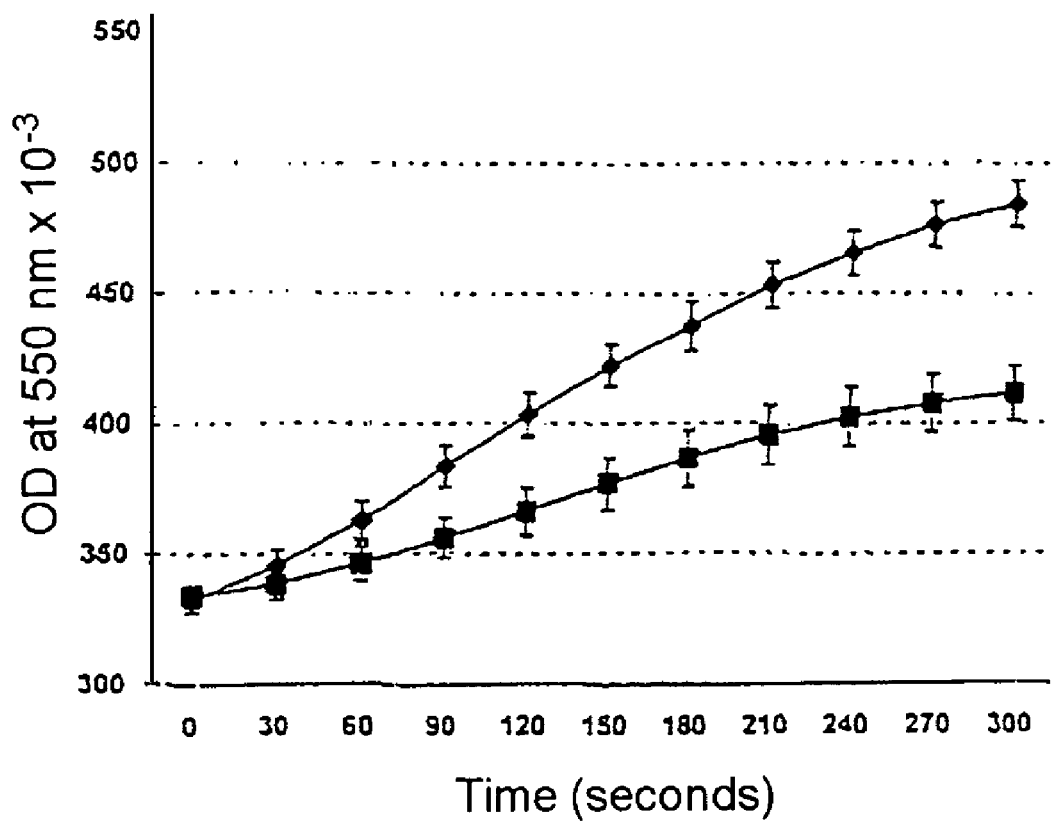
FIG. 1 describes the SOD-mimectic activity of Mangafodipir.

A subject of the present invention is the use of Mangafodipir for producing a medicinal product intended for the preventive or curative treatment of hepatocellular deficiency.

A set of pathological manifestations resulting from the destruction of hepatocytes are included under the term "hepatocellular deficiency". Depending on the extent of the cellular destruction, these clinical manifestations are more or less serious and reversible. In extreme cases, the massive and sudden destruction of the hepatocytes results in acute hepatic failure, also referred to as fulminant hepatitis, which can lead to death in a few days.

Among the most common causes of hepatocyte destruction which can lead to hepatocellular deficiency, mention will in particular be made of viral infections due to the various types of hepatitis virus, and also poisoning, in particular with certain medicinal products or with alcohol.

Several animal models of hepatocellular deficiency of various origins are currently available, which make it possible in particular to experimentally induce acute hepatic failure, and to study the mechanisms resulting in cellular destruction. Various mechanisms involving oxygenated free radicals have thus been proposed.

For example, acute hepatic failure of toxic origin, induced in particular by acetaminophen, is the result of saturation of the normal mechanisms of hepatic detoxification. In fact, at pharmacological doses, acetaminophen is mainly eliminated by glucuro- and sulfo-conjugation, but it is also oxidized by cytochrome P450 to N-acetyl-p-benziquinonimine (NAPQI), which can normally then be eliminated after conjugation with glutathione. In the event of overdose, saturation of the glucoro- and sulfo-conjugation pathways and increased production of NAPQI are observed [Prescott, Drugs, 25, 290-314, (1983)]. This very reactive metabolite is supposed to be the main effector of the hepatocyte damage, and the drug treatments proposed are based essentially on the use of antioxidants, such as N-acetyl-L-cysteine, the aim of which is to allow reconstitution of the intracellular glutathione stores and neutralization of NAPQI. The effectiveness of these treatments is, however, inconsistent [Caraceni and Van Thiel, Lancet, 345, 163-169, (1995); Schiodt et al., N. Engl. J. Med., 337, 1112-1117, (1997)] and, in the case of fulminant hepatitis, a liver transplant currently constitutes the only really effective treatment.

In the case of alcohol-induced hepatocellular deficiency, several mechanisms have been proposed, which mechanisms involve in particular the generation of toxic metabolites such as acetaldehyde, the superoxide anion or hydrogen peroxide.

The inventors have tested the effect of Mangafodipir on acute hepatic failure of toxic origin, using an experimental model of acute hepatic failure induced by administering acetaminophen. They have thus noted that the administration of Mangafodipir makes it possible to very significantly increase the survival rate after administration of a lethal dose of acetaminophen and to considerably reduce the toxic effects thereof. It therefore appears that Mangafodipir very effectively protects the hepatocytes against the destructive effects of toxic substances, and thus exerts an effect which is both preventive and curative on hepatocellular deficiency, in particular of toxic origin (drug-induced or alcohol-induced).

In addition, the inventors noted that the beneficial effects of Mangafodipir are observed not only when it is administered in a preventive capacity, but also when it is administered in a curative capacity, i.e. after the appearance of the first hepatotoxic effects.

According to a preferred embodiment of the present invention, the Mangafodipir is used for producing a medicinal product intended for the preventive or curative treatment of hepatocellular deficiency of toxic origin, and in particular for the treatment of acetaminophen-induced hepatocellular deficiency or of alcohol-induced hepatocellular deficiency.

Mangafodipir can in particular be used for producing a medicinal product intended for the treatment of acute hepatocellular deficiency, which manifests itself in particular in the form of fulminant hepatitis.

The glutathione reductase activity of Mangafodipir, which makes it possible to regenerate the intracellular glutathione pool, advantageously supplements its SOD activity and its catalase activity, in particular in the context of the treatment of acute hepatic failure of toxic origin, for example that induced by acetaminophen.

For implementing the present invention, the Mangafodipir will generally be used in formulations for administering a dose of active principle of between 0.1 and 10 mg/kg/day (preventive administration) or between 5 and 50 mg/kg/day (curative administration); higher doses may, however, be used given the low toxicity of this product. It is clearly understood that those skilled in the art can adjust these doses as a function of the particularities of each patient and of the pathological condition concerned.

In the context of the implementation of the present invention, the Mangafodipir can be administered by different routes. Generally, it will be administered orally or via injections, in particular subcutaneous, intramuscular or intravenous injections. Other routes of administration may be envisioned if they increase the effectiveness, the bioavailability or the tolerance of the products.

The present invention will be understood more clearly from the further description which follows, which refers to nonlimiting examples demonstrating the SOD, catalase and glutathione reductase activities of Mangafodipir and its effects, in vitro and in vivo, on hepatocellular deficiency.

EXAMPLE 1

Sod-Mimetic Activity of Mangafodipir

The SOD activity of a chemical compound can be determined by the NBT (nitro blue tetrazolium) reduction method according to the technique described by Beauchamp and Fridovich [Anal. Biochem., 44(1), 276-87, (1971)].

The test is carried out at 25° C. in a final volume of buffer of 0.8 ml (50 mM TRIS/HCl, pH 7.6), containing 22 µM of xanthine, 500 U/ml of catalase and 0.2 U/ml of xanthine oxidase. The reduction of NBT, in the presence of 1.5 µg of Mangafodipir or, as a control, in the absence of Mangafodipir, is measured every 30 seconds for 5 minutes. One SOD unit (U SOD) is defined by the amount of enzyme capable of inhibiting the NBT reduction rate by 50%.

The results are given in FIG. 1.

The legend for FIG. 1:

♦: Control

■: Mangafodipir (1.5 µg)

They show that the rate of reduction of NBT decreases from 0.0302/minute to 0.01556 when 1.5 µg of Mangafodipir is added to the reaction mixture. Based on these results, the SOD activity of the Mangafodipir was evaluated at 680 U SOD per milligram of Mangafodipir.

EXAMPLE 2

Catalase-Mimetic Activity of Mangafodipir

The catalase activity was assayed according to the method described by AEBI [Methods Enzymol., 105, 121-126, (1984)]. The decrease in optical density (OD) at 240 nm of a solution of 10 mM $H_2O_2$ in phosphate buffer (50 mM of $Na_2HPO_4/KH_2PO_4$, 0.1 mM EDTA, pH 7.4) was measured in the presence of 75.7 µg of Mangafodipir or, by way of reference, in the presence of 1 unit of bovine catalase.

Under these conditions, the catalase activity of Mangafodipir was evaluated at 2 U catalase per milligram of Mangafodipir.

EXAMPLE 3

Glutathione Reductase-Mimetic Activity of Mangafodipir

The glutathione reductase activity was assayed using the kit: "Glutathione reductase assay kit" marketed by the company Calbiochem. The reaction mixture is analyzed by spectrophotometry at 340 nm for 5 minutes.

The glutathione reductase activity of the Mangafodipir was evaluated at 19.9±1.75 mU glutathione reductase per milligram of Mangafodipir.

EXAMPLE 4

Protective Activity of Mangafodipir on Hepatocytes in Culture Subjected to the Action of the Superoxide Anion $O_2^-$ The Hep 3B human hepatic cell line was used for these experiments.

The cells were seeded in a 96-well culture plate, in a proportion of $5 \times 10^4$ cells per well, in a final volume of 50 µl.

One hundred µl of Mangafodipir solution at various concentrations (62.5, 125, 250 µg/ml) were deposited into each well (three wells per concentration tested). After incubation for one hour, 50 μl of a solution of xanthine at 200 μM and of 2 U/ml of xanthine oxidase (X/XO solution) were deposited into each well. Ten wells received no X/XO solution and served as controls to evaluate the baseline viability of the cells. Twelve hours after the X/XO solution had been deposited, the cells were washed with a saline solution and the viability was determined using an MTT test. A 0.2% MTT solution was deposited into each well and incubated for 4 hours at 37° C. The cells were then washed and the test was revealed by adding 50 μl of dimethyl sulfoxide (DMSO) to each well. The plates were then read on a spectrophotometer at a wavelength of 550 nm.

Figure 2:
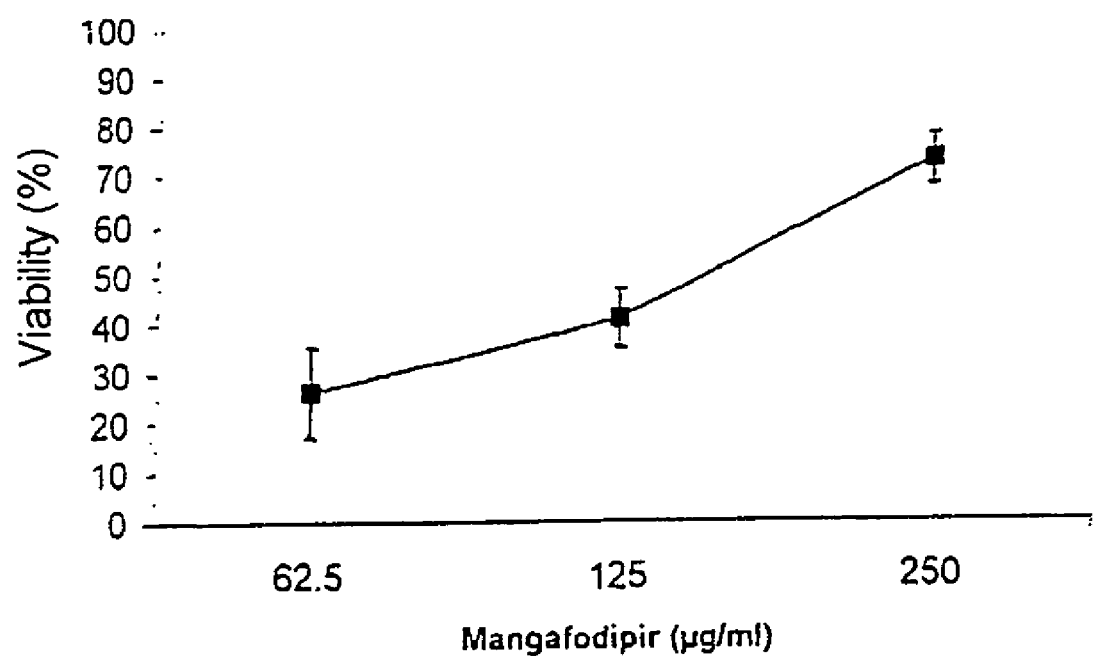
FIG. 2 shows results describing the protective activity of Mangafodipir on hepatocytes in culture subjected to the action of superoxide anion.

The results (percentage viable as a function of the Mangafodipir concentration) are given in FIG. 2.

These results show that the addition of Mangafodipir prevents the mortality of hepatic cells subjected to an oxidative stress mediated by the superoxide anion.

EXAMPLE 5

Protective Activity of Mangafodipir on Hepatocytes in Culture Subjected to the Action of Hydrogen Peroxide ($H_2O_2$)

The Hep 3B human hepatic cell line was also used for these experiments.

The cells were seeded in a 96-well culture plate, in a proportion of $5 \times 10^4$ cells per well, in a final volume of 50 μl. One hundred μl of Mangafodipir solution at various concentrations (62.5, 125, 250 μg/ml) were deposited into each well (three wells per concentration tested). After incubation for one hour, 50 μl of a solution of $H_2O_2$ at 4 mM were deposited into each well. Ten wells did not receive any $H_2O_2$ and served as controls to evaluate the baseline viability of the cells. Twelve hours after the solution of $H_2O_2$ had been deposited, the cells were washed with a saline solution and the viability was determined using an MTT test, as described in example 4 above.

Figure 3:
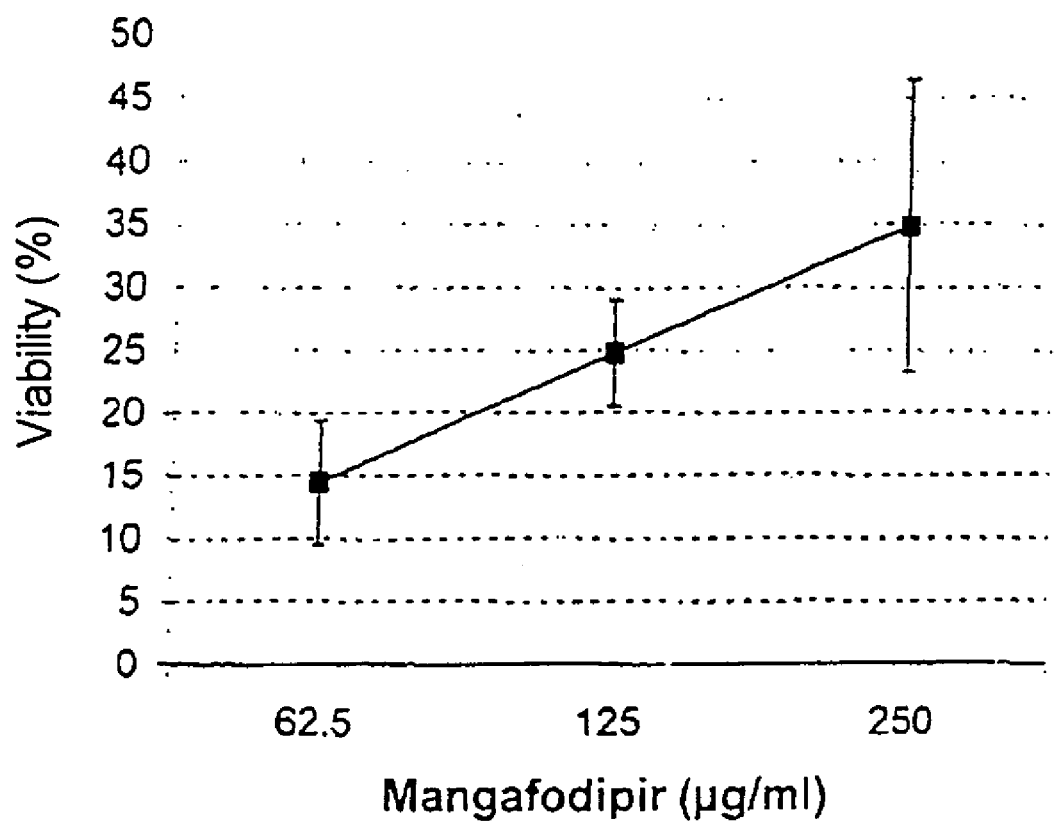
FIG. 3 shows results describing the protective activity of Mangafodipir on hepatocytes in culture subjected to the action of hydrogen peroxide.

The results (percentage viability as a function of the Mangafodipir concentration) are given in FIG. 3.

These results show that the addition of Mangafodipir prevents the mortality of hepatic cells subjected to an oxidative stress mediated by hydrogen peroxide.

EXAMPLE 6

Activity of Mangafodipir on Acetaminophen-Induced Acute Hepatic Failure

Intraperitoneal injection of acetaminophen into mice induces severe hepatotoxicity, the degree of which can be evaluated by animal survival and macroscopic and microscopic examination of the livers.

Animal Survival

The Mangafodipir (marketed under the name TESLASCAN™ by Nicomed-Amersham) is administered in the form of a bolus, intraperitoneally.

The acetaminophen (APAP), in solution at 100 mg/ml in PBS, at pH 7.4, is administered intraperitoneally.

In a first series of experiments, one group of mice was given a dose of 1000 mg/kg of acetaminophen; a second group was given a dose of 1000 mg/kg of acetaminophen, and a dose of 10 mg/kg of Mangafodipir administered either 2 h before the acetaminophen, or 6 h after; a control group was given Mangafodipir alone (10 mg/kg), or PBS alone.

Animal survival was monitored for 24 hours after the administration of acetaminophen.

| Group I: | PBS |
|---|---|
| Group II: | 1000 mg/kg of APAP |
| Group III: | 1000 mg/kg of APAP + 10 mg/kg of Mangafodipir, preventive |
| Group IV: | 1000 mg/kg of APAP + 10 mg/kg of Mangafodipir, curative. |

The results (number of surviving animals) are summarized in table I below:

TABLE 1

| | Time (hours) | | | | | | | | | | | | | | | |
|---|---|---|---|---|---|---|---|---|---|---|---|---|---|---|---|---|
| | 0 | 6 | 8 | 9 | 10 | 11 | 12 | 13 | 14 | 15 | 16 | 17 | 18 | 20 | 22 | 24 |
| Group I (n = 16) | 16 | 16 | 16 | 16 | 16 | 16 | 16 | 16 | 16 | 16 | 16 | 16 | 16 | 16 | 16 | 16 |
| Group II (n = 12) | 12 | 12 | 10 | 9 | 8 | 6 | 5 | 5 | 4 | 4 | 4 | 3 | 3 | 3 | 2 | 2 |
| Group III (n = 12) | 12 | 12 | 12 | 12 | 11 | 11 | 11 | 10 | 10 | 10 | 9 | 9 | 9 | 9 | 8 | 8 |
| Group IV (n = 12) | 12 | 12 | 11 | 11 | 10 | 9 | 9 | 8 | 8 | 8 | 7 | 7 | 7 | 6 | 6 | 5 |

These results show that 24 hours after the injection of acetaminophen, 16% of the animals intoxicated with APAP at the dose of 1000 mg/kg are dead, whereas the survival rate is greater than 41% in the animals intoxicated with APAP but given Mangafodipir after the administration of acetaminophen (curative protocol), and about 66% in the animals given Mangafodipir before the administration of acetaminophen (preventive protocol). No deaths are observed in the animals given the PBS alone.

Histological Study

In each of the groups, the livers of several animals were removed in order to perform a histological study. In the case of the mice given acetaminophen, considerably fewer apoptotic lesions are observed in the animals treated with Mangafodipir than in the animals not treated. No apoptotic lesion is visible in the mice of the control group not given acetaminophen.

EXAMPLE 7

Comparison of the Activities of Mangafodipir, of MnTBAP and of CuDIPS on Acetaminophen-Induced Acute Hepatic Failure CuDIPS (Cu[II]-[diisopropylsalicylate]) is a reference CuZnSOD mimetic (McKenzie et al., Br. J. Pharmacol. 127, 1159-1164, (1999)]; MnTBAP (Mn(III)-tetrakis(5,10,15,20-benzoic acid)-porphyrin) is an MnSOD mimetic which also has catalase activity and glutathione peroxidase activity (Application PCT/WO 01/12327). The effect of CuDIPS and of MnTBAP on the survival of mice after intraperitoneal injection of 1000 mg/kg of acetaminophen (APAP) was compared with that of Mangafodipir.

The experimental protocol is as follows:

The Mangafodipir, the MnTBAP or the CuDIPS are administered in the form of a bolus, in the preventive capacity, 2 hours before the acetaminophen.

Various groups of animals were given the following treatments:

| | |
|---|---|
| Group I: | PBS |
| Group II: | 1000 mg/kg of APAP |
| Group III: | 1000 mg/kg of APAP; 10 mg/kg of MnTBAP |
| Group IV: | 1000 mg/kg of APAP; 10 mg/kg of CuDIPS |
| Group V: | 1000 mg/kg of APAP; 10 mg/kg of Mangafodipir. |

Animal survival is monitored for 24 hours after the administration of acetaminophen.

The results, expressed as the number of surviving animals, are given in table II below.

TABLE II

| | Time (h) | | | | | | | | | | | | | | |
|---|---|---|---|---|---|---|---|---|---|---|---|---|---|---|---|
| | 0 | 6 | 8 | 9 | 10 | 11 | 12 | 13 | 14 | 15 | 16 | 17 | 18 | 20 | 22 | 24 |
| Group I (n = 16) | 16 | 16 | 16 | 16 | 16 | 16 | 16 | 16 | 16 | 16 | 16 | 16 | 16 | 16 | 16 | 16 |
| Group II (n = 12) | 12 | 12 | 10 | 9 | 8 | 6 | 5 | 5 | 4 | 4 | 4 | 3 | 3 | 3 | 2 | 2 |
| Group III (n = 12) | 12 | 12 | 12 | 12 | 11 | 10 | 10 | 10 | 9 | 9 | 8 | 8 | 8 | 8 | 7 | 7 |
| Group IV (n = 12) | 12 | 12 | 11 | 10 | 9 | 7 | 7 | 5 | 5 | 5 | 4 | 4 | 3 | 3 | 3 | 3 |
| Group V (n = 12) | 12 | 12 | 12 | 12 | 11 | 11 | 11 | 10 | 10 | 10 | 9 | 9 | 9 | 9 | 8 | 8 |

These results show that:
the Mangafodipir administered preventively increases the survival rate in a manner at least equal to the MnTBAP;
the CuDIPS does not significantly increase the survival rate.

Assaying Transaminases

In a second series of experiments, one group of mice was given a dose of 500 mg/kg of acetaminophen; a second group was given the same dose of acetaminophen, and a dose of 10 mg/kg of Mangafodipir administered 2 h before the acetaminophen; a third group of animals was given the same dose of acetaminophen, and a dose of 10 mg/kg of MnTBAP, and a fourth group of animals was given the same dose of acetaminophen, and a dose of 10 mg/kg of CuDIPS. The ASAT serum transaminases are assayed 12 hours after the administration of acetaminophen.

Figure 4:
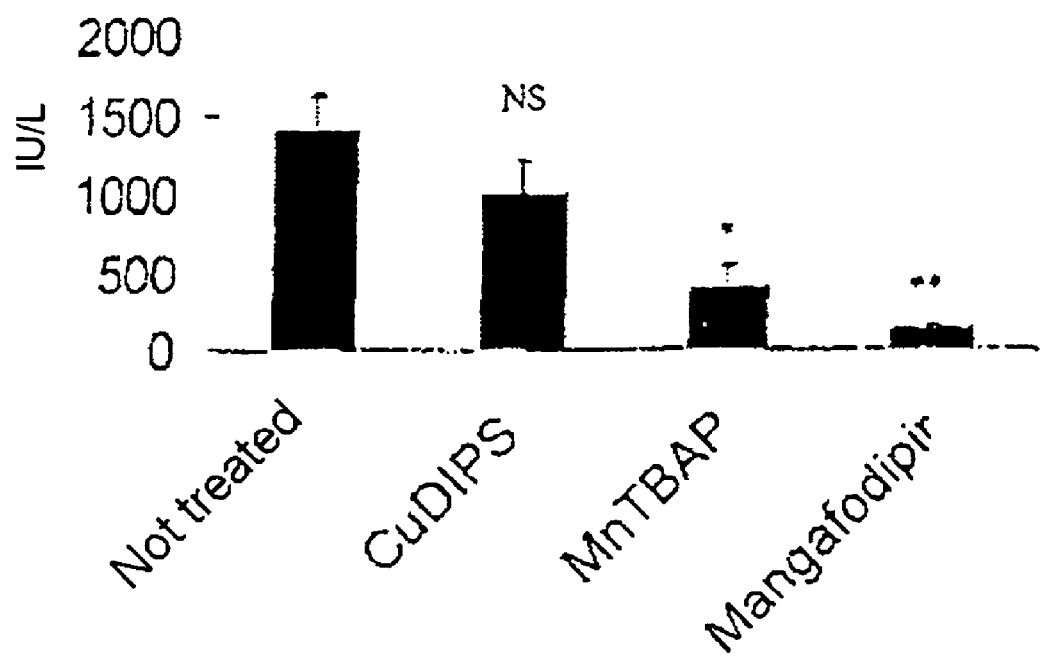
FIG. 4 shows results demonstrating that the administration of Mangafodipir decreases with transaminase activity.

The results are given in FIG. 4.
Legend for FIG. 4:
NS: not significant compared to the untreated mice
★: P<0.01 compared to the untreated mice
★★: P<0.001 compared to the untreated mice.

Among the mice given 500 mg/kg of acetaminophen ($APAP_{500}$), transaminase activities 10 times greater than in those which were given a pretreatment with Mangafodipir are observed after 12 hours.

These results show that, in all the cases, the administration of Mangafodipir decreases the transaminase activities, which reflect the hepatic cytolysis.

The invention claimed is:

1. A method for treating hepatocellular deficiency induced by alcohol or acetaminophen, consisting of administering mangafodipir to a patient in need thereof.

2. The method as claimed in claim 1, wherein said hepatocellular deficiency manifests itself in the form of fulminant hepatitis.

3. The method as claimed in claim 1, wherein said Mangafodipir is administered in a range comprised between 0.1 and 10 mg/kg/day.

4. The method as claimed in claim 1, wherein said Mangafodipir is administered in a range comprised between 5 and 50 mg/kg/day.

5. The method as claimed in claim 1, wherein said Mangafodipir is administered orally.

6. The method as claimed in claim 1, wherein said Mangafodipir is administered via injection.

7. The method as claimed in claim 6, wherein said Mangafodipir is administered via subcutaneous injection.

8. The method as claimed in claim 6, wherein said Mangafodipir is administered via intramuscular injection.

9. The method as claimed in claim 6, wherein said Mangafodipir is administered via intravenous injection.

10. The method as claimed in claim 3, wherein said Mangafodipir is administered orally.

11. The method as claimed in claim 3, wherein said Mangafodipir is administered via injection.

12. The method as claimed in claim 4, wherein said Mangafodipir is administered orally.

13. The method as claimed in claim 4, wherein said Mangafodipir is administered via injection.

* * * * *